United States Patent [19]

Morejon

[11] Patent Number: 5,709,691
[45] Date of Patent: Jan. 20, 1998

[54] ENDOTRACHEAL TUBE CLEANING DEVICE

[76] Inventor: Orlando Morejon, 235 SW. 79th Ave., Miami, Fla. 33144

[21] Appl. No.: 613,277

[22] Filed: Mar. 11, 1996

[51] Int. Cl.⁶ ........................................ A61D 01/12
[52] U.S. Cl. .................... 606/106; 606/196; 128/207.14; 128/207.15
[58] Field of Search ................... 606/191, 192, 606/196, 198, 194, 108; 128/207.14, 207.15, 207.17

[56] References Cited

U.S. PATENT DOCUMENTS

| | | |
|---|---|---|
| 3,064,294 | 11/1962 | Stocking . |
| 3,398,417 | 8/1968 | Erwin ............................ 15/104.19 |
| 4,021,265 | 5/1977 | Guenther . |
| 4,723,549 | 2/1988 | Wholey et al. ..................... 606/194 |
| 4,762,125 | 8/1988 | Leiman et al. ................... 128/207.15 |
| 4,787,659 | 11/1988 | Durham . |
| 4,981,470 | 1/1991 | Bombeck, IV .................... 606/196 |
| 5,003,657 | 4/1991 | Boiteau . |
| 5,030,213 | 7/1991 | Rumberger . |
| 5,119,811 | 6/1992 | Inglis et al. ....................... 128/207.14 |
| 5,143,062 | 9/1992 | Peckham ........................... 128/207.14 |
| 5,217,474 | 6/1993 | Zacca et al. ....................... 606/159 |
| 5,259,371 | 11/1993 | Tonrey ............................... 128/207.14 |
| 5,259,377 | 11/1993 | Schroeder ......................... 128/207.14 |
| 5,353,787 | 10/1994 | Price .................................. 128/207.14 |
| 5,386,741 | 2/1995 | Rennex . |
| 5,423,760 | 6/1995 | Yoon . |
| 5,499,625 | 3/1996 | Frass et al. ........................ 128/207.14 |

Primary Examiner—Mickey Yu
Assistant Examiner—Justine R. Yu
Attorney, Agent, or Firm—Malloy & Malloy, P.A.

[57] ABSTRACT

An endotracheal tube cleaning device to be used in an endotracheal tube of the type that has a flow through passage with an interior wall surface that defines an interior diameter thereof. The endotracheal tube cleaning device includes an elongate tubular member with a length at least as long as the endotracheal tube and a diameter smaller than a corresponding diameter of the endotracheal tube. Defined within the elongate tubular member, and extending from generally a first end to a second end thereof, is a channel. The channel terminates in an outlet port connected in fluid flow communication with a resilient material bladder that is structure to inflate to a diameter sufficient to engage the interior wall surface of the endotracheal tube. Moreover, the resilient material bladder is covered with an expandable exterior sheath that completely contains the resilient material bladder in case of rupture and provides an exterior, generally abrasive surface that engages and thereby cleans the interior wall surface of the endotracheal tube when the resilient material bladder is inflated and the elongate tubular member is removed from an inserted orientation within the endotracheal tube.

15 Claims, 2 Drawing Sheets

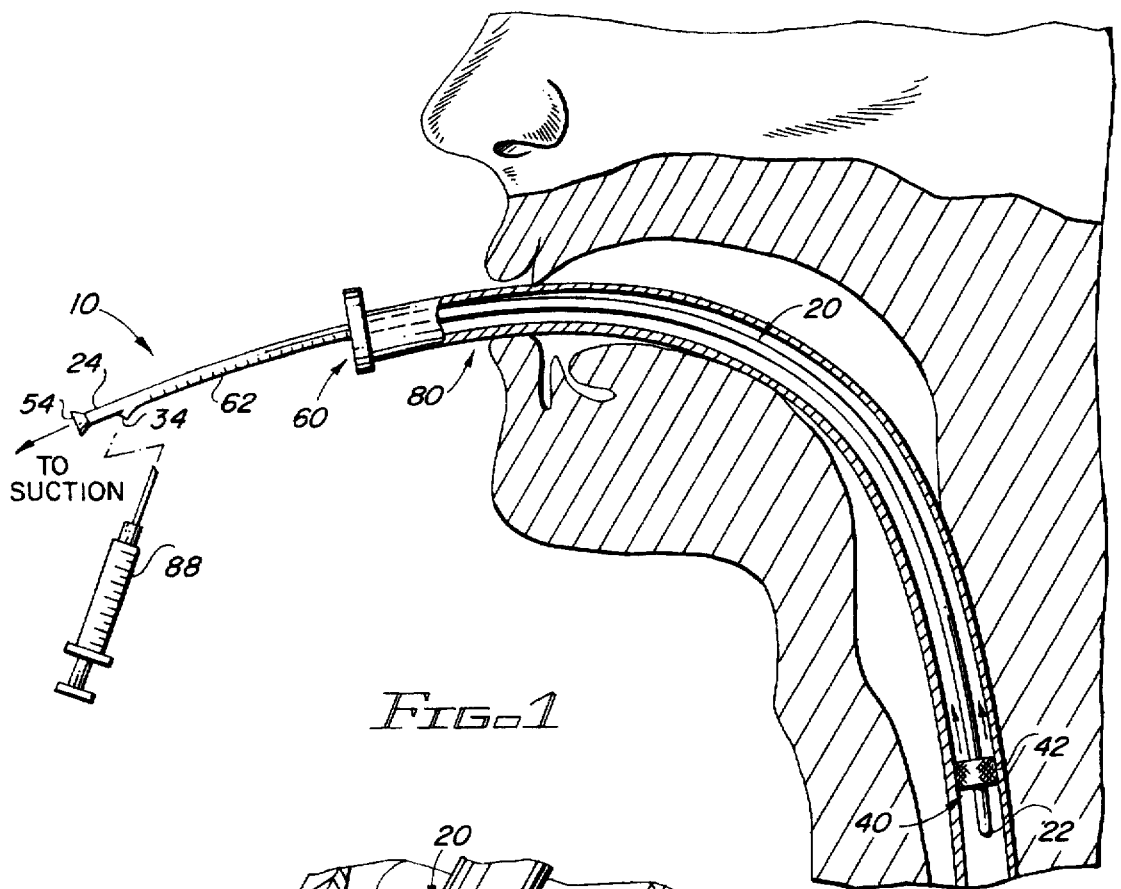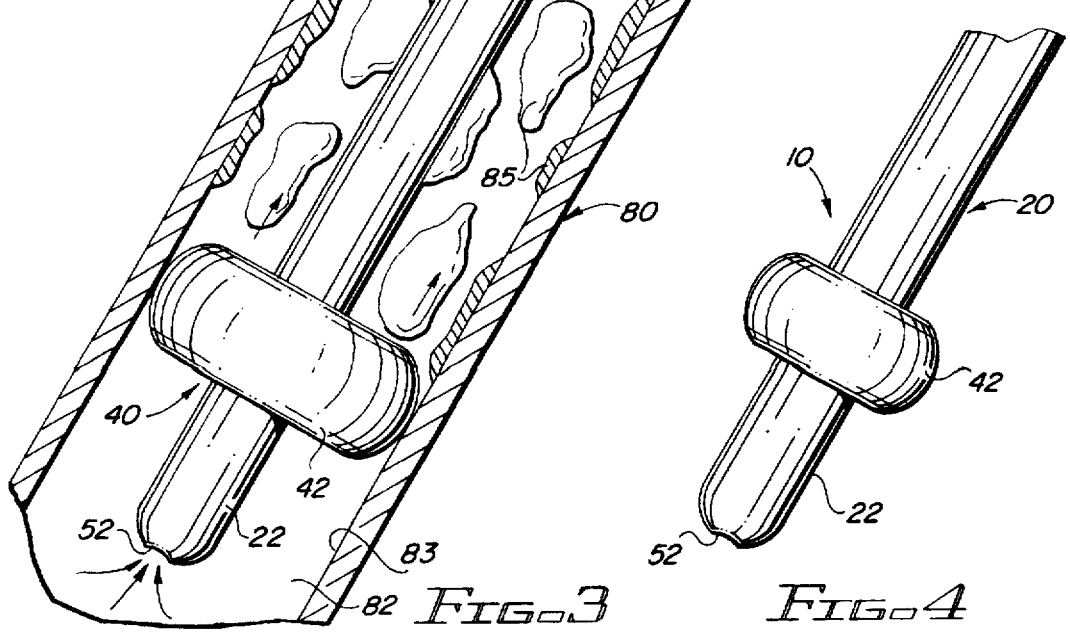

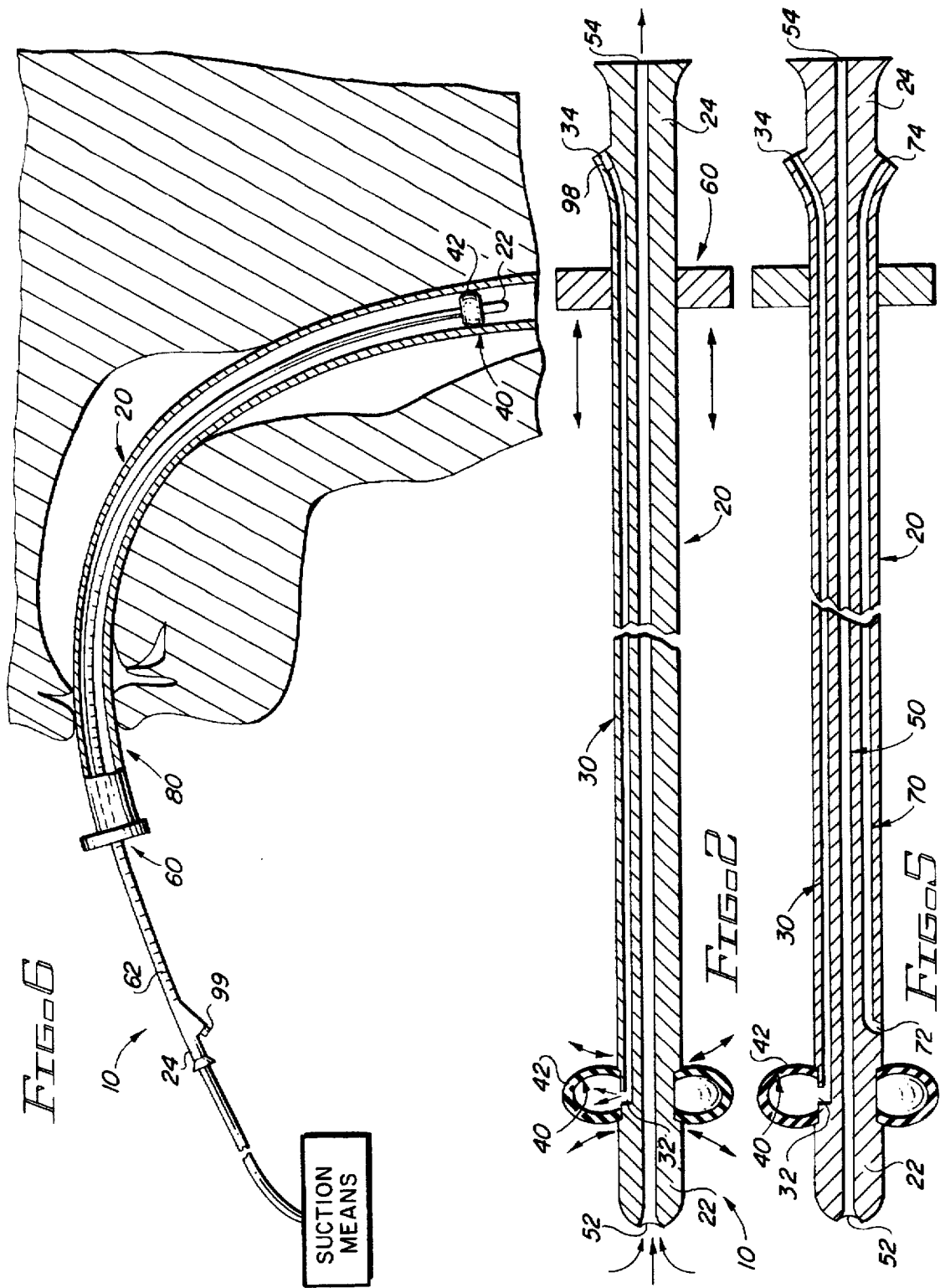

ENDOTRACHEAL TUBE CLEANING DEVICE

BACKGROUND OF THE INVENTION

1. Field of the Invention

The present invention relates to an endotracheal tube cleaning device to be used to effectively and efficiently clean the flow through passage of an endotracheal tube, without having to remove the endotracheal tube from the patient or significantly restricting airflow to the patient, and while effectively removing even solid buildup on the interior wall surface of the endotracheal tube safely and effectively.

2. Description of the Related Art

Many patients in a hospital, and in particular, patients in an Intensive Care Unit ("ICU") must be fitted with endotracheal tubes to facilitate their respiration. Specifically, an endotracheal tube is an elongate, semi-rigid lumen which is inserted into a patient's nose or throat and projects down into airflow communication with the patient's respiratory system. As such, the patient either directly, or with the aid of a respiratory unit, is able to breathe more effectively through the endotracheal tube.

Recent studies have determined, however, that the accumulation of dried tracheobronchial secretions on the interior wall surface of an operating endotracheal tube effectively decreases the lumen cross section, and thereby significantly increases the work of breathing for the intubated patient. Moreover, increasing the work of breathing for the patient necessitates that a higher level of support be provided to compensate, and often results in the patient's intubation period and ICU stay being significantly prolonged. Furthermore, it is also seen that thick secretions on the walls of the endotracheal tube often serve as a nidus for continued infection in the lungs, leading to added morbidity and hospital cost for the intubated patient.

To date, the only effective means of eliminating the accumulated secretions within an endotracheal tube completely, has been to exchange the contaminated endotracheal tube for a new tube. There are, however, several disadvantages to this procedure, such as temporary arrest of ventilatory support and the risk of complete loss of airway control. For example, re-intubation may be exceedingly difficult to patients with swelling of the soft tissue of the neck, and in patient's having cervical spine immobilization, because upon removal of the endotracheal tube the appropriate internal passages tend to close up and be otherwise difficult to isolate for reintroduction of a new endotracheal tube. Further, re-intubation of a patient can result in additional trauma to the oral, laryngeal and tracheal tissues.

Short of replacing the endotracheal tube completely, the only other means currently in use for maintaining endotracheal tubes somewhat clear is the use of flexible suction/irrigation catheters. Specifically, these suction/irrigation catheters, are passed down the endotracheal tube and upper airways and seek to evacuate contaminants from the lumen. Unfortunately, although the suction/irrigation catheters generally clear the airway of watery secretions, they are ineffective at clearing the inspissated secretions that have accumulated on the inner wall surface of the endotracheal tube over the course of days. In essence, the use of a suction/irrigation catheter merely delays the inevitable, namely, that the endotracheal tube be removed and replaced.

One somewhat recent attempt to address the problems associated with the maintenance of endotracheal tubes is seen to provide a two part assembly which is introduced into the flow through passage of the endotracheal tube. Specifically, a thin interior, solid segment having a plurality of retracting bristles and a sealing gasket at an end thereof is contained within an exterior lumen. In use, the entire coupled assembly is introduced into the endotracheal tube, but the interior segment is pushed through the outer tube so that the bristles expand to engage the wall surface, and the gasket member, such as a foam cylinder or balloon, expands to completely seal off the area behind the bristles. The entire device, including the upwardly angled bristles is then pulled upwardly with the gasket element completely sealing off the tube there below so that any debris removed by the bristles is retained. Such a device, however, does not provide for accurate and adjustable over-insertion limitation into the endotracheal tube, and completely seals off the endotracheal tube during removal so as to result in a potentially hazardous negative pressure or suction behind the cleansing device. Furthermore, it is seen from the need to include the bristles, that direct engagement of a gasket type member, such as the balloon, with the interior wall surface of the endotracheal tube, does not provide for any removal of secretions due to the smooth exterior surface of the gasket, but rather results in substantial friction between the rubbery gasket and the rubbery wall surface, thereby making is quite difficult to smoothly and effectively pull the cleansing device from the endotracheal tube. Additionally, it is seen that upwardly angled bristle members are susceptible to complete or partial retraction as they encounter obstacles and attempt to scrape clean the interior of the endotracheal tube, and in fact, the bristle members are often quite sharp and may be damaging to the endotracheal tube or to a patient if inadvertently projected beyond the endotracheal tube so that the outwardly projecting bristle members become stuck outside the endotracheal tube. Also, because of the collapsing configuration of bristles, gaps will naturally exist between adjacent bristles and some areas of the tube are not engaged. Moreover, such a device which includes interlocked interior and exterior portions and has a fixedly disposed outwardly depending flange does not permit the replacement of an endotracheal tube thereover, nor does it permit the effective introduction of a guide wire for endotracheal tube replacement. Similarly, such a single function device necessitates that additional items be introduced into the tube, generally resulting in additional trauma to the patient, if some suction is necessary.

As such, there is still a substantial need in the art for a cleaning device that can be used to clear endotracheal tube secretions effectively on a regular basis, thereby expediting ventilatory weaning and extubation of ICU patients. Further, there is a need for an effective endotracheal tube cleaning tube which can be easily and effectively introduced into the endotracheal tube, and which can be easily removed, even though it effectively removes solid secretion buildup, due to its friction minimizing engagement with the interior wall surface of the endotracheal tube and/or because of its alleviation of negative pressure/suction within the endotracheal tube upon removal thereof. Additionally, there is a need for a cleaning device which can be accurately extended into the endotracheal tube without substantial risk of over introduction, will not become lodged through the endotracheal tube in the event that it protrudes slightly from the end of the endotracheal tube, and which can be utilized for multiple functions such as an effective guide for the reintroduction of a new or cleaned endotracheal tube.

SUMMARY OF THE INVENTION

The present invention is directed towards an endotracheal tube cleaning device to be used to clean an endotracheal tube of the type including a flow through passage with an interior wall surface that defines an interior diameter thereof. Specifically, the endotracheal tube cleaning device includes an elongate tubular member having a diameter smaller than the interior diameter of the endotracheal tube. Further, the elongate tubular member includes a first end and a second end, and is structured of a length at least equivalent to a length of the endotracheal tube.

Defined within the elongate tubular member, and extending from generally its first end to its second end is a channel. The channel provides a fluid flow through conduit and terminates in an outlet port defined in the elongate tubular member, generally near the second end thereof.

Secure the elongate tubular member, also generally at the second end thereof is a resilient material bladder. The resilient material bladder is specifically structured to inflate to a diameter sufficient to engage the interior wall surface of the endotracheal tube with some pressure. Further, the resilient material bladder is disposed in fluid flow communication with the outlet port of the channel. As such, fluid exiting the channel through the outlet port is directed into the resilient material bladder for subsequent inflation thereof. Additionally, disposed about the resilient material bladder is an expandable, exterior sheath. Specifically, the exterior sheath is structured to completely contain the resilient material bladder in case of rupture. Furthermore, the expandable, exterior sheath provides an exterior, generally abrasive surface that engages, and thereby cleans, the interior wall surface of the endotracheal tube upon the resilient material bladder being inflated and the elongate tubular member being removed from an inserted orientation within the flow through passage of the endotracheal tube.

It is an object of the present invention to provide an endotracheal tube cleaning device which can efficiently and easily be routinely utilized to maintain the flow through passage of an endotracheal tube free from the accumulation of dried tracheobronchial secretions.

Further, an object of the present invention is to provide an endotracheal tube cleaning device which can easily and effectively be oriented so as to prevent over insertion into endotracheal tubes of varying lengths.

Yet another object of the present invention is to provide an endotracheal tube cleaning device which can absorb watery secretions as well as remove dried secretions from the interior wall surface of an endotracheal tube.

Also an object of the present invention is to provide an endotracheal tube cleaning device which provides sufficient abrasion to remove dried secretions from the interior wall surface, but which is also substantially smooth and easy to slidingly remove from the endotracheal tube while it is engaged with the interior wall surface thereof.

Another object of the present invention is to provide an endotracheal tube cleaning device which can provide effective cleaning pressure on the interior wall surface on the endotracheal tube, but which provides minimal risk of external contamination through the rupture of a resilient material bladder thereof.

A further object of the present invention is to provide an endotracheal tube cleaning device which can alleviates negative pressure deep within the endotracheal tube when the cleaning device is made to engage the wall surface of the endotracheal tube for cleansing thereof.

Another object of the present invention is to provide an endotracheal tube cleaning device which can be effectively utilized as a guide for the removal and replacement of an endotracheal tube into a patient.

Still another object of the present invention is to provide an endotracheal tube cleaning device which can simultaneously provide abrasive dried secretion removal with effective suction/irrigation to remove watery secretions.

Also an object of the present invention is to provide an endotracheal tube cleaning device which permits the introduction of a guide wire for effective removal and replacement of an endotracheal tube thereover into the patient.

Yet another object of the present invention is to provide an endotracheal tube cleaning device which can be utilized to perform a variety of functions during a single insertion.

Another object of the present invention is to provide an endotracheal tube cleaning device which can be utilized to suction a patients airway and will not harm the patient if inserted beyond the tube for that purpose.

BRIEF DESCRIPTIONS OF THE DRAWINGS

For a fuller understanding of the nature of the present invention, reference should be had to the following detailed description taken in connection with the accompanying drawings in which:

FIG. 1 is a side view of the endotracheal tube cleaning device of the present invention in an operative orientation within an endotracheal tube;

FIG. 2 is a side cross-sectional view of the endotracheal tube cleaning device of the present invention;

FIG. 3 is an isolated side view of the resilient material bladder and exterior sheath in an operative, cleaning position within an endotracheal tube;

FIG. 4 is an isolated view of the endotracheal tube cleaning device of the present invention illustrating the orientation of the resilient material bladder and expandable exterior sheath when not in an operable, cleaning orientation; and FIG. 5 is a side cross-sectional view of another embodiment of the endotracheal tube cleaning device of the present invention;

Like reference numerals refer to like parts throughout the several views of the drawings.

FIG. 6 is a side view of an alternative embodiment of the endotracheal tube cleaning device of the present invention with only a portion of the exterior sheath including an abrasive surface.

DETAILED DESCRIPTION OF THE PREFERRED EMBODIMENT

Shown throughout the Figures, the present invention is directed toward an endotracheal tube cleaning device, generally indicated as 10. In particular, the endotracheal tube cleaning device 10 is constructed for use with an endotracheal tube 80 that is conventionally utilized to enable a patient to breathe, and as such, is generally inserted down the throat of a patient as illustrated in FIG. 1. Such an endotracheal tube 80 is preferably of the type including a flow through passage 82 having an interior wall surface 83 that defines its interior diameter. Generally, after prolonged periods of use, the endotracheal tube 80 will exhibit a buildup of secretions 85 that form on the interior wall surface 83 and can thereby obstruct airflow through the flow through passage 82. The endotracheal tube cleaning device 10 of the present invention is structured to facilitate the removal of those secretions 85 in a convenient and effective manner.

In particular, the endotracheal tube cleaning device 10 of the present includes an elongate tubular member 20 having a first end and a second end. The elongate tubular member 20, which is preferably of a semirigid construction so as to allow it to bend and conform to the operative configuration of the endotracheal tube 80 within a patient, has a length at least equivalent to a length of the endotracheal tube 80. As such, the endotracheal tube cleaning device 10 can effectively reach deep down into the length of the endotracheal tube 80 for effective cleaning of even the most remotely introduced portions thereof. Furthermore, the elongate tubular member 20 is structured with a diameter smaller than the interior diameter of the endotracheal tube 80, and in fact, is preferably quite narrow so as to facilitate the introduction of the elongate tubular member 20 into endotracheal tubes of varying sizes. Moreover, the elongate tubular member 20 is preferably configured so as to be useable through a Y-connector implemented at an exposed end of an endotracheal tube 80 and structured to permit the continuance of air flow through one inlet of the Y-connector, while permitting introduction of the elongate tubular member 20 through the other inlet of the Y-connector.

Defined within the elongate tubular member 20 is a channel 30. Specifically, the channel 30 is structured to extend from generally the first end 24 of the elongate tubular member 20 towards the second end 22 of the elongate tubular member 20. Moreover, the channel 30 will terminate in an outlet port 32 defined generally near the second end 22 of the elongate tubular member 20. The outlet port 32 of the channel 30 is structured and disposed so as to permit the escape of a fluid, such as air, therethrough, subsequent to its passage through the length of elongate tubular member 20 within the channel 30. As illustrated in the preferred embodiment of the drawings, the outlet port 32 of the channel 30 preferably extends out a side of the elongate tubular member 20, near the second end 22 of the elongate tubular 20, and may preferably extend into an annular track defined in the elongate tubular member 20.

Secured to the elongate tubular member 20, also generally at the second end 22 thereof is a resilient material bladder 40. Preferably the resilient material bladder 40 engages the elongate tubular member 20 within the annular track, and as such is disposed over the outlet port 32 of the channel 30. Accordingly, the resilient material bladder 40 is structured and disposed to be in fluid flow communication with the outlet port 32 and hence the channel 30. Therefore, when a fluid, such as air, exits the channel 30 through the outlet port 32, it will pass into the resilient material bladder 40 to result in a corresponding inflation thereof. Specifically, the resilient material bladder 40 is formed of an expandable material and is structured to inflate to at least a diameter sufficient to engage the interior wall surface 83 of the endotracheal tube 80 with some pressure. Additionally, the resilient material bladder 40 may be sized to be variably inflated and thereby permit effective use of the endotracheal tube cleaning device 10 within endotracheal tubes 80 having varying interior diameters. The resilient material bladder 40 may be secured to the elongate tubular member 20 in a variety of fashions, and may take on a variety of configurations effective to provide for appropriate inflation and secure retention at generally the second end 22 of the elongate tubular member 20. By way of example, the resilient material bladder 40 can have an inner-tube type configuration secured to the elongate tubular member 20 and having inlet opening connected in fluid flow communication with the outlet port 32 of the channel 30. Alternatively, the resilient material bladder 40 can have a tire-type configuration wherein the resilient material 40 has a generally C-shaped cross section and forms a seal between its edges and the exterior surface of the elongate tubular member 20 in order to captivate air therebetween for the resultant inflation of the resilient material bladder 40.

Disposed at least partially, but preferably completely about the resilient material bladder 40 is an expandable, exterior sheath 42. In the preferred embodiment, the expandable exterior sheath 42 is specifically structured and disposed to completely contain the resilient material bladder 40, and thereby prevent passage of any portion of the resilient material bladder 40 down into the endotracheal tube 80 should the resilient material bladder 40 rupture during inflated use. Furthermore, the expandable, exterior sheath provides an exterior, generally abrasive surface which will engage and thereby clean the entire interior wall surface 83 of the endotracheal tube 80 when the resilient material panel 40 is inflated. Preferably, the expandable exterior sheath 40 has a soft, expandable mesh type configuration which can engage an entire circumference of the interior wall surface 83. As such, when the resilient material bladder 40 is collapsed, as illustrated in FIG. 4, the expandable exterior sheath 42 is also collapsed, but does not sag or droop. Rather, the gaps within the mesh type configuration of the expandable exterior sheath 42 will merely reduce and the mesh will normally maintain its more tightly packed mesh configuration. Alternatively, however, when the resilient material bladder 40 is inflated, the expandable mesh type configuration of the expandable exterior sheath 42 permits it to stretch out and maintain its covering relation over the resilient material bladder 40. It is therefore seen, that the plurality of openings defined in the expandable exterior sheath 42, when it is expanded and wrapped about an inflated, operable resilient material bladder 40, provide a generally abrasive exterior surface that when passed over the interior wall surface 83 of the endotracheal tube 80 will function to loosen the secretions 85 that are stuck to the interior wall surface 83 of the endotracheal tube 80. Accordingly, effective cleaning results when the resilient material bladder 40 is inflated and the elongate tubular member 20 is pulled out from its inserted orientation within the flow through passage 82 of the endotracheal tube. It is also seen, however, that some in and out movement of the elongate tubular member 20 may be necessary to provide for complete and effective secretion 85 removal.

In addition to containing the resilient material bladder 40 in case of rupture, and providing the exterior, generally abrasive surface necessary for cleaning, the expandable exterior sheath 42, which may be formed of a nylon or other soft material mesh, also provides a smooth exterior surface that facilitates movement during introduction and removal of the resilient material bladder 40, and therefore the elongate tubular member 20, into and out of the endotracheal tube 80. Specifically, because of the material construction of the resilient material bladder 40, significant friction may be exhibited between the resilient bladder 40 itself, and the interior wall surface 83 of the endotracheal tube 80. Such frictional resistance may make it quite difficult, or at least quite erratic during the removal and/or reintroduction of the resilient material bladder 40 into the endotracheal tube 80. Furthermore, the expandable exterior sheath can more effectively absorb and/or remove the secretions if the resilient material bladder 40 can be retained in an inflated orientation as the endotracheal tube cleaning device 10 is completely removed from the endotracheal tube 80 because any dislodged secretions 85 are substantially prevented from dropping beneath the resilient material bladder 40 where they may fall into the patient.

Disposed opposite the outlet port 32 of the channel 30, and also connected in fluid flow communication with the channel 30 is an inlet port 34. Specifically, the inlet port 34 is structured to permit the introduction of a fluid, preferably air, into the channel 30 for subsequent inflation of the resilient material bladder 40. While this inlet port 34 may be positioned anywhere in the elongate tubular member 20, so long as it generally near the first end 24 thereof in order to permit the introduction of fluid therethrough when the elongate tubular member 20 is substantially introduced into the endotracheal tube 80, in the preferred embodiment inlet port 34 is operatively disposed at a slight angle from an axis of the elongate tubular member 20. Specifically, this orientation of the inlet port 34 is structured to permit facilitated introduction of air into the channel 30, such as through the use of a hypodermic syringe. Accordingly, the inlet port 34 of the channel 30 will preferably include valve means structured to restrict the escape of fluid after the resilient material bladder has been filled. Although such valve means are not absolutely necessary, especially in circumstances were a hypodermic syringe is merely introduced into the channel through the inlet port 34, and it functions to prevent the escape of air and the deflation of the resilient material bladder 40, in the preferred embodiment, and so as to permit the removal of the hypodermic syringe 88 or other fluid introduction medium during cleaning, the valve means are included. As such, the valve means may merely include a resilient material stopper 98 which permits the penetration of a needle of the hypodermic syringe 88 therethrough, but seals up to prevent the escape of air therethrough upon removal of the hypodermic syringe 88. Also, the valve means may include a more complex valve type element with a stopper 99 that is actuated by a user of the endotracheal tube cleaning device 10 and connects directly with a hub of the hypodermic syringe body.

Further included in the endotracheal tube cleaning device 10 of the present invention is an adjustable stopper element 60. This adjustable stopper element 60 which may be formed in a variety of configurations out of a variety of materials is structured to be slidably disposed about the elongate tubular member 20, generally at the first end 24 thereof. As such, the stopper element 60 has a diameter which is at least greater than the interior diameter of the flow through passage 82 of the endotracheal tube 80. In use, the adjustable stopper element 60 is slidably oriented along a length of the elongate tubular member 20 so as to prevent over insertion of the elongate tubular member 20 into the endotracheal tube. In particular, it is generally not favorable for the second end 22 of the elongate tubular member 20 to penetrate beyond an open end of the endotracheal tube 80, as it may come in contact with interior organs and/or tissue of the patient. As such, upon knowing the dimension of the endotracheal tube 80 being utilized within the patient, the adjustable stopper element 60 is appropriately positioned to ensure that the second end 22 of the elongate tubular member 20 is not over inserted into the endotracheal tube 80. Furthermore, so as to further facilitate effective positioning of the adjustable stopper element 60, a gradiated indicia 62 is preferably disposed on an exterior surface of the elongate tubular member. Therefore, once a particular length of the endotracheal tube 80 is known, the stopper element 60 is effectively and easily positioned to prevent the over insertion.

In addition to being slidably positionable so as to prevent over insertion of the elongate tubular member 20 into the endotracheal tube 80, the stopper element 60 is preferably structured to be removable in certain circumstances. Specifically, the elongate tubular member 20 is preferably substantially narrow relative to an interior diameter of the endotracheal tube 80. As such, in certain circumstances wherein the endotracheal tube 80 is seen to be too contaminated to be effectively cleaned, or for any other clinical reason it is determined that the tube must be removed from the patient and replaced with a new endotracheal tube 80, the stopper element 60 may be easily removed from around the elongate tubular member 20, which is operatively inserted within the endotracheal tube 80, and the used endotracheal tube 80 can be effectively pulled out of the patient over the elongate tubular member 20. Specifically, in many circumstances after an endotracheal tube 80 is removed from a patient, the effective passages within the patient can become obstructed and/or otherwise difficult to relocate. By maintaining the elongate tubular member 20 within the patient and merely removing the endotracheal tube 80 thereover, reintroduction of a new endotracheal tube 80 is substantially facilitated. It is therefore seen, that while the stopper element 16 may be removed in a variety of fashions, it is preferred that the stopper element 60 have a generally disc type configuration, with a slot formed in the surface thereof, so as to permit facilitated widening thereof, and removal from its engaged position about the elongate tubular member 20.

Also in the preferred embodiment, the endotracheal tube cleaning device 10 of the present invention includes an equilibrium channel 50. Specifically, the equilibrium channel 50 is defined in the elongate tubular member 20 and is structured to extend from generally the first end 24 of the elongate tubular member 20 to generally the second end 22 of the elongate tubular member 20, at a point beyond the resilient material bladder 40. Accordingly, the equilibrium channel 50 will provide a passage that significantly alleviates suction/negative pressure behind the resilient material bladder 40 as it is being removed from the endotracheal tube 80 in its inflated orientation. It is understood, that when the resilient material bladder 40 is inflated it effectively forms a seal with the interior wall surface 83 of the endotracheal tube 80. Therefore, as the elongate tubular member 20 is pulled for cleaning, a suction effect behind the resilient material 40 can result. Not only can this suction effect make it substantially more difficult to remove the endotracheal tube cleaning device 10 from the endotracheal tube 80, but some trauma can result to the patient as a result of this suction effect and a loss of continued ventilation through the endotracheal 80 can result. Through the positioning of the equilibrium channel 50, the suction pressure is alleviated, and in fact, some air flow is permitted to the patient therethrough, if necessary.

Further, the equilibrium channel 50, which includes ports 52 and 54 at generally the first and second ends of the elongate tubular member 20, may also be configured to receive a guide wire therethrough which will function as an alternative guide for the removal and reintroduction of an endotracheal tube 80 into the patient. Also, in the preferred embodiment, suction means may be connected with the equilibrium channel 50. Specifically, the suction means are structured and disposed to withdraw residue cleaned from the interior wall surface 83 of the endotracheal tube 80, and not captivated at or above the resilient material bladder 40 during cleansing. Moreover, the suction means can draw out watery secretions, which are generally more difficult to completely eliminate through the resilient material bladder 40 and expandable exterior sheath 42, through the equilibrium channel 50. Similarly, the suction means can function to suction a patients airway, beyond the endotracheal tube, in some circumstances, by introducing the second end 22 of the tubular member 20 beyond the endotracheal tube. Such multiple features permits additional tasks to be performed without having to introduce or re-introduce additional devices. With regard to the suction functions, it is understood that the port 52 of the equilibrium channel 50 may be disposed right at a tip of the second end 22 of the elongate tubular member 20, or may be disposed in a side wall of the elongate tubular member 20, and may in fact include more than one port 52 so as to provide for more effective suction within the endotracheal tube 80. Further, it is also understood that the equilibrium channel 50 may be divided into a pair of channels, one to provide for suction and another to provide for alleviation of removal resisting suction pressure behind the resilient material bladder 40.

In an additional embodiment of the endotracheal tube cleaning device 10 of the present invention, yet another elongate passage 70 may extend through the elongate tubular member 20. This elongate passage 70 includes an inlet opening 74 disposed at the first end 24 of the elongate tubular member, and an outlet opening 72 disposed generally at the second end 22 of the elongate tubular member 20. Preferably, the outlet opening 72 will be disposed above the resilient material bladder 40 such that during cleaning suction can be applied above the resilient material bladder 40 to remove any loosened debris and/or fluid that may affect or hinder the cleaning process of the resilient material bladder 30. In this embodiment, the equilibrium channel 50 may be used to maintain respiratory air flow to the patient during cleaning. It will also be appreciated that the inlet opening 74 may be configured in any manner including the manners in which inlet port 34 is configured.

While this invention has been shown and described in what is considered to be a practical and preferred embodiment, it is recognized that departures may be made within the spirit and scope of this invention which should, therefore, not be limited except as set forth in the claims which follow and within the doctrine of equivalents. Furthermore, it is noted that the device of the present invention may also be utilized with similar medical tubes, such as a thoracostomy tube.

Now that the invention has been described, What is claimed is:

1. An endotracheal tube cleaning device to be used in an endotracheal tube including a flow through passage having an interior wall surface which defines an interior diameter of the endotracheal tube, said endotracheal tube cleaning device comprising:

an elongate, tubular member having a length at least equivalent to a length of the endotracheal tube and a diameter smaller than the interior diameter of the endotracheal tube, said elongate tubular member including a first end and a second end, a channel defined in said elongate tubular member and extending from a vicinity of said first end of said elongate tubular member towards said second end of said elongate tubular member, said channel terminating in an outlet port defined in said elongate tubular member, at said vicinity of said second end thereof, a resilient material bladder secured to said elongate tubular member, at said vicinity of said second end thereof, and structured to be inflated to at least approximately said interior diameter of the endotracheal tube, said resilient material bladder being disposed in fluid flow communication with said outlet port of said channel such that fluid exiting said channel through said outlet port inflates said resilient material bladder, and an expandable, exterior sheath disposed about and structured to completely encase said resilient material bladder so as to contain said resilient material bladder in case of rupture, said exterior sheath being structured and disposed to substantially conform to said resilient material bladder, upon inflation thereof, and thereby engage the interior wall surface of the endotracheal tube so as to define an exterior, abrasive surface which affirmatively engages the interior wall surface of the endotracheal tube, under an outward, inflated pressure of said resilient material bladder, and thereby applies cleaning pressure to the interior wall surface of the endotracheal tube upon said elongate tubular member being removed from an inserted orientation within the flow though passage of the endotracheal tube.

2. An endotracheal tube cleaning device as recited in claim 1 wherein said expandable exterior sheath includes a soft, expandable, mesh configuration having a plurality of openings formed therein which provide said exterior, generally abrasive surface and are structured to facilitate smooth introduction and removal of said resilient material bladder and therefore said elongate, tubular member into and out of the endotracheal tube.

3. An endotracheal tube cleaning device as recited in claim 1 further including an adjustable stopper element slidably disposed about said elongate tubular member, generally at said first end thereof, said stopper element having a diameter greater than the interior diameter of the flow through passage of the endotracheal tube such that over-insertion of said elongate tubular member into the endotracheal tube is prevented thereby.

4. An endotracheal tube cleaning device as recited in claim 3 wherein said stopper element is removable so as to enable the endotracheal tube to be removed from within a patient over said elongate tubular member introduced therein, and thereby enable said elongate tubular member to remain in place within the patient so as to facilitate appropriate replacement of a new endotracheal tube into the patient over said elongate tubular member.

5. An endotracheal tube cleaning device as recited in claim 3 wherein said elongate tubular member includes a gradiated indicia disposed thereon, said gradiated indicia being structured to facilitate positioning of said stopper element in an appropriate over-insertion limiting position by providing a reference guide to be compared against the length of the endotracheal tube.

6. An endotracheal tube cleaning device as recited in claim 1 wherein said channel includes an inlet port and valve means, said valve means being structured and disposed to restrict the escape of fluid from said inlet port of said channel.

7. An endotracheal tube cleaning device as recited in claim 1 wherein said channel is structured for coupled engagement with a hypodermic syringe so as to facilitate the introduction of air into said channel and therefore into said resilient material bladder.

8. An endotracheal tube cleaning device as recited in claim 1 further including an equilibrium channel extending from generally said first end of said elongate, tubular member to generally said second end of said elongate tubular member at a point beyond said resilient material bladder, said equilibrium channel being structured and disposed to alleviate suction pressure behind said resilient material bladder upon removal of said elongate tube from the endotracheal tube with said resilient material bladder in an inflated, tube cleaning orientation, and to permit air flow to the patient upon said resilient material bladder being disposed in an inflated orientation.

9. An endotracheal tube cleaning device as recited in claim 8 further including a guidewire, said equilibrium channel being further structured to receive said guide wire therethrough, and said guide wire being structured and disposed to guide the removal and re-introduction of the endotracheal tube into the patient.

10. An endotracheal tube cleaning device as recited in claim 8 further including suction means connected with said equilibrium channel, said suction means being structured and disposed to withdraw residue cleaned from the interior wall surface of the endotracheal tube and not captivated at or above said resilient material bladder.

11. An endotracheal tube cleaning device as recited in claim 8 further including an elongate passage extending through said elongate tubular member from generally said first end thereof to said second end thereof, said elongate passage including an outlet opening disposed in said elongate tubular member above said resilient material bladder.

12. An endotracheal tube cleaning device as recited in claim 1 wherein said elongate, tubular member is generally narrow so as to facilitate introduction into endotracheal tubes of varying interior diameters.

13. An endotracheal tube cleaning device as recited in claim 1 wherein said tubular member is semi-rigid.

14. An endotracheal tube cleaning device as recited in claim 1 further including an elongate passage extending through said elongate tubular member from generally said first end thereof to said second end thereof, said elongate passage including an outlet opening disposed in said elongate tubular member above said resilient material bladder.

15. An endotracheal tube cleaning device to be used in an endotracheal tube including a flow through passage having an interior wall surface which defines an interior diameter of the endotracheal tube, said endotracheal tube cleaning device comprising:

an elongate, tubular member having a diameter smaller than the interior diameter of the endotracheal tube, a channel defined in said elongate tubular member, said channel terminating in an outlet port defined in said elongate tubular member, a resilient material bladder coupled to said elongate tubular member in fluid flow communication with said outlet port, said resilient material bladder being structured to be inflated to at least approximately said interior diameter of the endotracheal tube and exert a quantity of pressure thereon, and an expandable, exterior sheath structured and disposed to completely enshroud said resilient material bladder so as to contain said resilient material bladder in case of rupture, and so as to substantially conform to said resilient material bladder upon inflation thereof and thereby affirmatively engage the interior wall surface of the endotracheal tube under said quantity of pressure exerted by said resilient material bladder and define an exterior abrasive surface structured to engage and thereby clean the interior wall surface of the endotracheal tube upon passage thereover.

* * * * *